US00PP33664P2

(12) United States Plant Patent
van de Pol

(10) Patent No.: US PP33,664 P2
(45) Date of Patent: Nov. 23, 2021

(54) ***GAULTHERIA* PLANT NAMED 'GSW1600201'**

(50) Latin Name: *Gaultheria procumbens*
Varietal Denomination: GSW1600201

(71) Applicant: Peter van de Pol, Wilp (NL)

(72) Inventor: Peter van de Pol, Wilp (NL)

(73) Assignee: Genius Genes Production Facilities B.V., Wilp (NL)

( * ) Notice: Subject to any disclaimer, the term of this patent is extended or adjusted under 35 U.S.C. 154(b) by 0 days.

(21) Appl. No.: 17/230,795

(22) Filed: Apr. 14, 2021

(51) Int. Cl.
*A01H 5/00* (2018.01)
*A01H 6/36* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of *Gaultheria* plant named 'GSW1600201', characterized by its compact and uniformly mounding to rounded plant habit; moderately vigorous growth habit and moderate to rapid growth rate; freely branching habit; dark green-colored leaves; freely flowering and freely fruiting habit; white-colored flowers and white-colored fruits that typically do not "pink" during low light and low temperatures conditions.

2 Drawing Sheets

Figure 1:
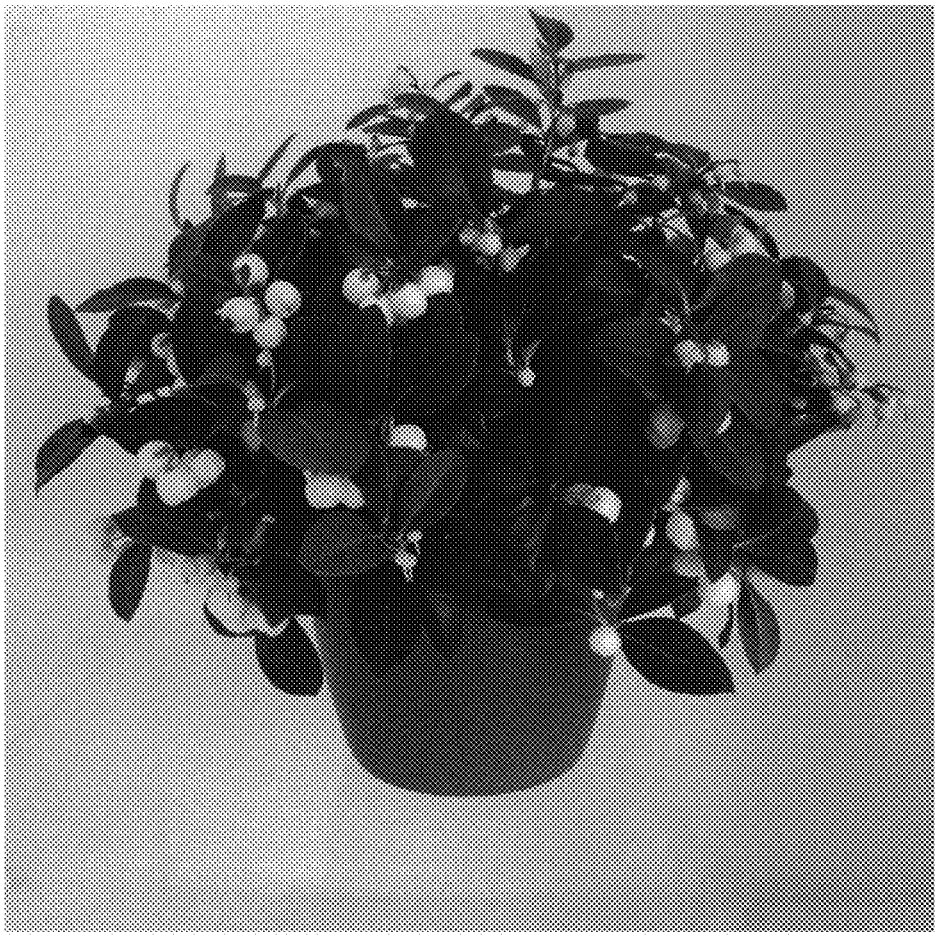

Botanical designation: *Gaultheria procumbens.*
Cultivar denomination: 'GSW1600201'.

STATEMENT REGARDING PRIOR DISCLOSURES BY THE INVENTOR/APPLICANT & ASSIGNEE

An European Community Plant Breeder's Rights application for the instant plant was filed by the Genius Genes Production Facilities B.V. of Wilp, The Netherlands on Feb. 27, 2018, application number 2018/0627. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Gaultheria* plant, botanically known as *Gaultheria procumbens*, commonly referred to as Wintergreen and hereinafter referred to by the name 'GSW1600201'.

The new *Gaultheria* plant is a product of a planned breeding program conducted by the Inventor in Twello, The Netherlands. The objective of the breeding program is to create new uniform and compact *Gaultheria* plants with numerous flowers and fruits.

The new *Gaultheria* plant originated from a self-pollination conducted by the Inventor in Twello, The Netherlands in July, 2014 of a proprietary selection of *Gaultheria*

*procumbens* identified as code number 1000-8, not patented. The new *Gaultheria* plant was discovered and selected by the Inventor as a single flowering plant from within the progeny of the stated self-pollination in a controlled greenhouse environment in Twello, The Netherlands in October, 2015.

Asexual reproduction of the new *Gaultheria* plant by in vitro meristem culture in a controlled greenhouse environment in Twello, The Netherlands since May, 2016 has shown that the unique features of this new *Gaultheria* plant are stable and reproduced true to type in successive generations.

SUMMARY OF THE INVENTION

Plants of the new *Gaultheria* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'GSW1600201'. These characteristics in combination distinguish 'GSW1600201' as a new and distinct *Gaultheria* plant:

1. Compact and uniformly mounding to rounded plant habit.
2. Moderately vigorous growth habit and moderate to rapid growth rate.
3. Freely branching habit.
4. Dark green-colored leaves.
5. Freely flowering and freely fruiting habit.
6. White-colored flowers and white-colored fruits that typically do not "pink" during low light and low temperatures conditions.

Plants of the new *Gaultheria* can be compared to plants of the parent selection. Plants of the new *Gaultheria* differ primarily from plants of the parent selection in the following characteristics:

1. Plants of the new *Gaultheria* are more compact than plants of the parent selection.
2. Plants of the new *Gaultheria* are more freely flowering and freely fruiting than plants of the parent selection.

Plants of the new *Gaultheria* can also be compared to plants of *Gaultheria procumbens* 'SPECGP11', disclosed in U.S. Plant Pat. No. 27,170. In side-by-side comparisons, plants of the new *Gaultheria* differ primarily from plants 'SPECGP11' in the following characteristics:

1. Plants of the new *Gaultheria* are more rounded and not as flat-topped as plants of 'SPECGP11'.
2. Plants of the new *Gaultheria* have larger leaves than plants of 'SPECGP11'.

BRIEF DESCRIPTION OF THE PHOTOGRAPHS

The accompanying colored photographs illustrate the overall appearance of the new *Gaultheria* plant showing the colors as true as it is reasonably possible to obtain in colored reproductions of this type. Colors in the photographs may differ slightly from the color values cited in the detailed botanical description which accurately describe the actual colors of the new *Gaultheria* plant.

The photograph on the first sheet (FIG. 1) comprises a side perspective view of a typical flowering plant of 'GSW1600201' grown in a container.

Figure 2:
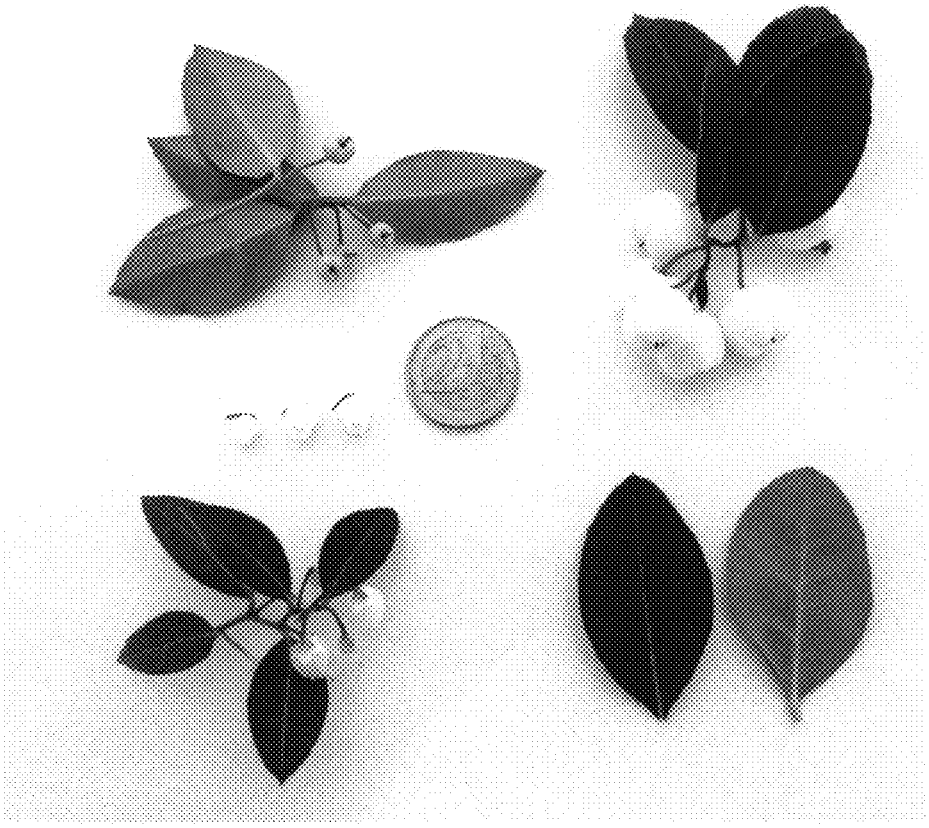

The photograph on the second sheet (FIG. 2) is a close-up view of the upper and lower surfaces of typical leaves, developing flowers, fully developed flowers and developing fruits of 'GSW1600201'.

DETAILED BOTANICAL DESCRIPTION

The aforementioned photographs and following observations, measurements and values describe plants grown during the early autumn in 15-cm containers in a glass-covered greenhouse in Twello, The Netherlands and under cultural practices typical of commercial *Gaultheria* production. During the production of the plants, day temperatures ranged from 10° C. to 15° C. and night temperatures ranged from 4° C. to 10° C. Plants were 22 months old when the photographs and description were taken. In the following description, color references are made to The Royal Horticultural Society Colour Chart, 2015 Edition, except where general terms of ordinary dictionary significance are used.

Botanical classification: *Gaultheria procumbens* 'GSW1600201'.

Parentage:

*Female, or seed, parent*.—Proprietary selection of *Gaultheria procumbens* identified as code number 1000-8, not patented.

*Male, or pollen, parent*.—Proprietary selection of *Gaultheria procumbens* identified as code number 1000-8, not patented.

Propagation:

*Type*.—By in vitro meristem culture.

*Time to initiate roots, winter*.—About one to two weeks at temperatures about 18° C. to 19° C.

*Time to produce a rooted young plant, winter*.—About three months at temperatures of 4° C. and higher.

*Root description*.—Fine, fibrous; typically white to brown in color, actual color of the roots is dependent on substrate composition, water quality, fertilizers, substrate temperature and physiological age of roots.

*Rooting habit*.—Moderately freely branching; medium density.

Plant description:

*Plant and growth habit*.—Perennial evergreen shrub; compact and uniformly mounding to rounded plant habit; moderately vigorous growth habit and moderate to rapid growth rate.

*Plant height, soil level to top of foliar plane*.—About 18.1 cm.

*Plant height, soil level to top of floral plane*.—About 16.9 cm.

*Plant diameter* (*spread*).—About 36.3 cm.

*Lateral branch description*.—Branching habit: Freely branching habit, typically about 20 primary lateral branches each with typically five secondary lateral branches developing per plant. Length: About 13.5 cm. Diameter: About 1.5 mm. Internode length: About 9.5 mm. Aspect: Primary lateral branches, about erect to horizontal and secondary lateral branches, about 50° from primary branch axis. Strength: Strong. Texture and luster: Densely pubescent; developing stems are matte becoming slightly glossy with development. Color, developing: Close to 145B; at the internodes, close to 148C variably tinged with close to 182A. Color, developed: Close to 147D variably tinged with close to 181C and 182B; with development, color becoming closer to 182B; when woody, close to 164A and 165B.

Leaf description:

*Arrangement*.—Alternate, simple.

*Length*.—About 4.9 cm.

*Width*.—About 2.7 cm.

*Shape*.—Elliptic.

*Apex*.—Acute.

*Base*.—Attenuate.

*Margin*.—Coarsely and shallowly serrate.

*Texture and luster, upper surface*.—Smooth, mostly glabrous except for main vein which is pubescent; not rugose; coriaceous; slightly glossy.

*Texture and luster, lower surface*.—Smooth, glabrous; not rugose; coriaceous; very slightly glossy.

*Venation pattern*.—Pinnate.

*Color*.—Developing leaves, upper surface: Close to 143B. Developing leaves, lower surface: Close to 146D. Full expanded leaves, upper surface: Darker than between 139A and N189A; venation, close to 144B. Fully expanded leaves, lower surface: Close to 146B; venation, close to 145C.

*Petioles*.—Length: About 6 mm. Diameter: About 2 mm. Strength: Strong. Texture and luster, upper and lower surfaces: Densely pubescent; matte. Color, upper surface: Close to 145A to 145B variably tinged with close to 181A. Color, lower surface: Close to 145C variably tinged with close to 184C.

Flower description:

*Flower type and flowering habit*.—Terminal flowers arranged in short racemes with typically three to four flowers per inflorescence, and axillary flowers are single; flowers urceolate in shape and nodding; freely flowering habit with about 650 flower buds and flowers develop per plant during the flowering season.

*Natural flowering season*.—Plants flower continuously from spring into the autumn in The Netherlands; plants begin to flower about 20 to 25 weeks after planting.

*Flower longevity on the plant*.—About one week; flowers not persistent.

*Fragrance*.—None detected.

*Inflorescence size*.—About 1.9 cm by 2.2 cm.

*Flower buds*.—Length: About 7 mm. Diameter: About 6 mm. Shape: Broadly ovoid. Texture and luster: Smooth, glabrous; slightly glossy. Color: Immature sepals, close to 155B and immature petals, close to NN155C.

*Flowers*.—Diameter: About 8 mm by 8 mm. Depth (length): About 1 cm.

*Petals*.—Quantity and arrangement: Five petals arranged in a single whorl; lower 87.5% portion of the petals are fused. Length: About 9 mm. Width, free part: About 2 mm. Shape, free part: Ovate. Apex: Broadly and bluntly acute, recurved. Margin: Entire; not undulate. Texture and luster, upper surface: Smooth, glabrous; not rugose; velvety; matte. Texture and luster, lower surface: Smooth, glabrous; not rugose; moderately velvety; matte. Color: When opening and fully opened, upper surface: Close to NN155D; venation, close to NN155D; color does not change with development or conditions. When opening and fully opened, lower surface: Close to NN155D; venation, close to NN155D; color does not change with development or conditions.

*Sepals*.—Quantity and arrangement: Five sepals arranged in a single whorl; lower half fused. Length: About 4 mm. Width: About 2.5 mm. Shape, free part: Ovate, slightly concave. Apex: Acute. Margin: Entire. Texture and luster, upper and lower surfaces: Smooth, glabrous; matte. Color: When opening and fully opened, upper surface: Close to NN155A. When opening and fully opened, lower surface: Close to NN155A.

*Peduncles*.—Length: About 7 mm. Diameter: About 1.25 mm. Strength: Strong. Aspect: Continuous with lateral branch. Texture and luster: Densely pubescent; matte. Color: Close to 151C variably tinged with close to 182C.

*Pedicels*.—Length: About 1.2 cm. Diameter: About 7.5 mm. Strength: Strong. Aspect: About 50° from peduncle axis. Texture and luster: Densely pubescent; matte. Color: Close to 150B to 150C variably tinged with close to 183C.

*Reproductive organs*.—Stamens: Quantity per flower: Typically ten; basifixed. Filament length: About 3 mm. Filament color: Close to NN155A. Anther size: About 0.5 mm by 1.5 mm. Anther shape: Narrowly oblong, fringed at the apex. Anther color: Close to 165B; towards the apex, close to 165D. Pollen amount: Scarce. Pollen color: Close to 164D. Pistils: Quantity: Typically one. Pistil length: About 5 mm. Style length: About 4.5 cm. Style color: Close to 155C. Stigma diameter: About 0.5 mm. Stigma shape: Narrowly club-shaped. Stigma color: Close to 150D. Ovary color: Close to 146D.

*Fruits*.—Quantity: One per flower; about 650 fruits develop per plant during the autumn in The Netherlands. Length: About 1.3 cm. Diameter: About 1.6 cm. Fragrance: When crushed, wintergreen fragrance. Texture: Smooth, glabrous. Color, when developing: Close to 145A. Color, developed: Close to NN155C; fruits typically do not "pink" during low light and low temperatures conditions.

*Seeds*.—Quantity: Numerous seeds per fruit, dust-like. Length: Less than 0.2 mm. Diameter: Less than 0.2 mm. Texture: Smooth, glabrous. Color: Close to 164C.

Pathogen & pest resistance: To date, plants of the new *Gaultheria* have not been noted to be resistant to pathogens and pests common to *Gaultheria* plants.

Temperature tolerance: Plants of the new *Gaultheria* have been observed to tolerate temperatures of about −23° C. to 35° C. and to be suitable for USDA Hardiness Zones 5 through 9.

It is claimed:

1. A new and distinct *Gaultheria* plant named 'GSW1600201' as illustrated and described.

* * * * *